United States Patent [19]

Lovas et al.

[11] Patent Number: 5,593,965
[45] Date of Patent: Jan. 14, 1997

[54] ANTI-TUMOR EFFECTS OF GNRH-III

[75] Inventors: Sandor Lovas; J. Michael Conlon, both of Omaha, Nebr.; Borbala Vincze, Budapest, Hungary; Istvan Palyi, Budapest, Hungary; Dezso Gaal, Budapest, Hungary; Adrienn Kalnay, Budapest, Hungary; Imre Mezo, Budapest, Hungary; Istvan Teplan, Budapest, Hungary; Geza Toth, Szeged, Hungary; Magdolna Kovacs, Pecs, Hungary

[73] Assignee: Creighton University, Omaha, Nebr.

[21] Appl. No.: 326,710

[22] Filed: Oct. 20, 1994

[51] Int. Cl.⁶ ................................................ A61K 38/00
[52] U.S. Cl. ................................................................ 514/15
[58] Field of Search ................................................ 514/15

[56] References Cited

PUBLICATIONS

Deragon et al, General and Comparative Endocrinology, 95, 363–367 (1994) (Sep.).

Primary Examiner—Jerome D. Goldberg
Attorney, Agent, or Firm—Benjamin A. Adler

[57] ABSTRACT

The present invention provides a novel pharmaceutical composition for the treatment of breast cancer. Also provided are various methods of treating breast cancer.

4 Claims, 3 Drawing Sheets

ANTI-TUMOR EFFECTS OF GNRH-III

BACKGROUND OF THE INVENTION

1. Field of the Invention

The present invention relates generally to the fields of molecular endocrinology and peptide chemistry. More specifically, the present invention relates to a novel method of treating tumors using GnRH-III.

2. Description of the Related Art

Gonadotropin-Releasing Hormone (GnRH; also known as Luteinizing Hormone Releasing Hormone or LHRH) is a major hypothalamic peptide hormone responsible for stimulating the release of Luteinizing Hormone and Follicle Stimulating Hormone from the anterior pituitary. The primary structure of GnRH has been determined in, inter alia, mammals, salmon, catfish, chicken, and most recently, lamprey.

Lamprey GnRH differs in five amino acids compared with salmon GnRH, dogfish GnRH and chicken GnRH-II. A second form of GnRH exists in lamprey and this form (GnRH-II) differed from lamprey GnRH-I by three residues (Ile, Phe and His instead of Glu, Lys, and Tyr). More recently, a third immunoreactive form of lamprey GnRH has been discovered, lamprey GnRH-III.

Analogs of GnRH are known to inhibit the growth of mammary tumors and do so by two mechanisms: (1) estrogen deprivation; and (2) a direct effect on cancer cells. It is well known that gonadectomy is a necessary therapeutic intervention in the management of gonadal steroid dependent tumors. The GnRH analogs can exert their antitumor activity not only through chemical castration but also by directly affecting the tumor cells. The presence of GnRH binding sites in human mammary cancer cells has been previously reported. Mammary tumor cell membranes contain both high and low affinity binding sites. Moreover, human breast cancer cell lines, such as MDA-MB-231 and ZR-75-1, express the GnRH gene. GnRH analogs interact directly with mammary tumor and activate a G-protein dependent transducing mechanism. Previous studies indicated that the direct growth inhibition of mammary tumor cell lines is achieved with relatively high analog concentrations, e.g., $10^{-6}$ to $10^{-5}$M. The peptide levels correspond with apparent binding to low affinity receptors on the mammary cancer cells. According to the prior art, a GnRH antagonist (SB-75) interferes most likely with the autocrine loop of IGF-II and several levels, namely, IGF-II secretion, production of IGF-I binding proteins and the effect of IGF-II on cell growth.

The amino acid sequence of GnRH-III is known and was isolated from the sea lamprey, *Petromyzon marinus*. GnRH-III has 60% homology to mammalian GnRH. GnRH-III is the first peptide in the GnRH family which has an Asp residue at position six.

The prior art is deficient in the lack of effective means of inhibiting the growth and proliferation of mammary tumor cells and in treating breast cancer generally. The present invention fulfills this longstanding need and desire in the art.

SUMMARY OF THE INVENTION

In one embodiment of the present invention, there is provided a pharmaceutical composition, comprising a pharmacologically effective dose of Gonadotropin Releasing Hormone-III and a pharmaceutically acceptable carrier.

In another embodiment of the present invention, there is provided a method of a method of inhibiting the proliferation of mammary tumor cells, comprising the step of administering a pharmacologically effective dose of the pharmaceutical composition of the present invention to an individual in need of such treatment.

In yet another embodiment of the present invention, there is provided a method of a method of inhibiting the proliferation of mammary tumor cells, comprising the step of administering a pharmacologically effective dose of the pharmaceutical composition of the present invention and an antiestrogen.

In still yet another embodiment of the present invention, there is provided a method of treating a mammary carcinoma in an individual without significant corresponding loss of gonadal function, comprising the step of administering a pharmacologically effective dose of Gonadotropin Releasing Hormone-III.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
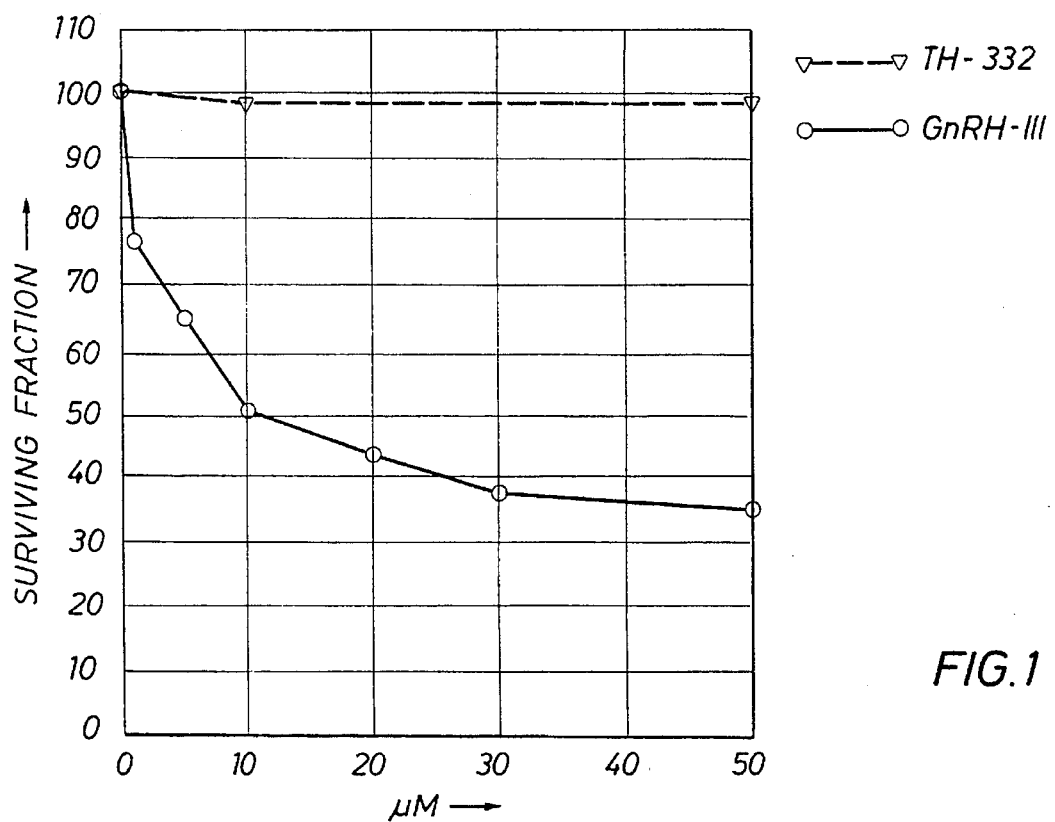
FIG. 1 shows the dose-response curves of MCF-7 cells (10% FCS) treated with GnRH analogs.

The present invention is directed to a pharmaceutical composition, comprising a pharmacologically effective dose of Gonadotropin Releasing Hormone-III and a pharmaceutically acceptable carrier. Generally, the pharmaceutical composition of the present invention may be administered in any dose which provide an inhibitory effect on mammary tumor cells. Preferably, the dose of Gonadotropin Releasing Hormone-III is from about 0.002 mg/kg to about 0.02 mg/kg.

The present invention is also directed to a method of inhibiting the proliferation of mammary tumor cells, comprising the step of administering a pharmacologically effective dose of the pharmaceutical composition of the present invention to an individual in need of such treatment. Preferably, the pharmaceutical composition is administered to a human.

The present invention also provides a method of inhibiting the proliferation of mammary tumor cells, comprising the step of administering a pharmacologically effective dose of the pharmaceutical composition of the present invention in combination with other anti-tumor compounds, e.g., an antiestrogen. Generally, any antiestrogen which synergizes with Gonadotropin Releasing Hormone-III is acceptable. Preferably, the antiestrogen is tamoxifen.

The present invention also encompasses a method of treating a mammary carcinoma in an individual without significant corresponding loss of gonadal function, comprising the step of administering a pharmacologically effective dose of Gonadotropin Releasing Hormone-III.

It is specifically contemplated that pharmaceutical compositions may be prepared using the novel peptide of the present invention. In such a case, the pharmaceutical composition comprises the novel peptide of the present invention and a pharmaceutically acceptable carrier. A person having ordinary skill in this art would readily be able to determine, without undue experimentation, the appropriate dosages and routes of administration of the novel peptide of the present invention.

Gonadotropin Releasing Hormone-III may not be orally active and consequently, one with ordinary skill in this art would readily recognize the necessity of administering GnRH-III by other means. Preferred means for administering GnRH-III is by (1) injection; (2) nasal spray or small particle aerosol nebulizer; (3) depot or suspension; or (4) infusion.

The pharmaceutical compositions of the present invention are suitable for use in a variety of drug delivery systems. For a brief review of present methods for drug delivery, see Langer, *Science*, 249:1527–1533 (1990). Methods for preparing administrable compounds will be known or apparent to those skilled in the art and are described in more detail, for example, in Remington's *Pharmaceutical Science*, 17th ed., Mack Publishing Company, Easton, Pa. (1988).

The following examples are given for the purpose of illustrating various embodiments of the invention and are not meant to limit the present invention in any fashion.

EXAMPLE 1

Synthesis of GnRH-III

The peptide was synthesized (0.25 mmol scale) using an Applied Biosystems model 430A peptide synthesizer on a 4-(1,1dimethoxyphenyl-Fmoc-aminomethyl)-phenoxy resin. All amino acids, except pyroglutamic acid, were N-α-Fmoc protected and were coupled as their 1-hydroxybenzotrizoic active esters. The reactive side chain groups were protected as follows: His, N-im-trityl; Asp, B-t-Butyl ester, Lys, N-t-Boc; Ser, t-Butyl ester. The peptide was cleaved from the resin by stirring with trifluoroacetic acid/1,2-ethanedithiol/anisole (95:1.6:3.4), by volume) for 90 minutes at room temperature. The yield of crude product was 280 mg.

EXAMPLE 2

Purification of GnRH-III

The synthetic peptide, GnRH-III was purified to apparent homogeneity by reverse phase high pressure liquid chromatography on a (1×50 cm) Vydac C-18 (15–20 µM) column equilibrated with 50 mM ammonium acetate, pH 4.5, at a flow rate of 5 ml/minute. The concentrtion of acetonitrile in the eluting solvent was raised to 33% (volume/volume) over 100 minutes. The identity of the peptide was confirmed by amino acid analysis: Asp 0.61(1), Glu 0.84 (1), Gly 0.99 (1), His 1.82 (2), Lys 1.00 (1), Pro 1.10 (1), Ser )0.66(1) and by low resolution fast atom bombardment mass spectrometry: $(M+H)^+=1259(1259.6)$.

EXAMPLE 3

Cancer cell lines

Two human breast cancer cell lines were used. They were: (1) the estrogen receptor positive MCF-7 cell line and (2) the estrogen receptor negative MDA-MB-231 cell line. Both cell lines contain GnRH receptors. These cell lines were used to illustrate the anticancer effects of GnRH-III. The cells were maintained in Dulbecco-modified Eagle-minimal essential medium (DMEM, GIBCO) containing 10% fetal calf serum (10% FCS).

EXAMPLE 4

Clonogenic assay

The clonogenic assay provides information on the cell damaging effects of a substance in a dose-dependent manner. Three hundred cells were transferred into 35 mm Petri dishes in 2.5 ml of medium. On the following day, the cultures were treated with 1, 5, 10, 20, 30 and 50 µM doses of GnRH-III. Colonies which developed from specific cells were stained with crystal violet and counted on days 8 to 12 after treatment. Colony numbers of untreated control cultures were counted for comparison.

EXAMPLE 5

Antiproliferation Assay

The antiproliferation assay used herein measures the inhibition of cell proliferation due to drug exposure. Loose subconfluent cultures ($6\times10^5$–$1\times10^6$ cells) in 100 mm Petri dishes were initiated and treated with 1, 5, 10, 20, 30 and 50 µM doses of GnRH-III on every other day for various periods of time. On day 6, the cell numbers of both control and treated cultures were counted in a Neubauer-type hemocytometer.

EXAMPLE 6

Chemical Castration

Adult female rates(Wistar-R-Amsterdam), 200–250 grams, housed under controlled lighting (light period 05:00 to 19:00) with free access to pelleted food and tap water were used herein. For the in vivo assay of inhibition of ovulation, aliquots of peptide solutions were injected subcutaneously into female rats at noon on the day of proestrous for single-dose tests and every day at noon for long term tests. Only rats which had previously shown three consecutive regular 4-day cycles, as indicated by vaginal smears test, were used herein. Animals were ovariectomized on the day of the first diestrous after the injection. Oviducts were prepared under stereo-microscope and tested for ova as is well known in the art.

EXAMPLE 7

In vitro Experiments

The GnRH activity of the peptides were assayed by using the superfused rat pituitary cell system as described by Vigh and Schally, *Peptides*, 5:241–247, Suppl. 1, (1984) and Csernus and Schally, *Neuroendocrine Research Methods*, Greenstein, B., ed., Harwood Academic Publishers, London, pp66–102 (1985). Mixed cell populations of four regularly cycling female rats, at random stages of the estrous cycle, were used in each chamber of a superfusion apparatus. The cells were perfused for 12 hours with Medium 199 (Sigma) at a flow rate of 20 ml/hour, prior to administration of the peptides. Pituitary cells were exposed to 9 minute pulses of the peptides at concentrations of 1, 10, 100 and 1000 μM rpior to 1 nM GnRH. The peptide-containing solutions are prepared from the stock solution immediately before use. At the beginning of each experiment, cells were rechallenged with potassium to check the secretability of Luteinizing Hormone, independent of the participation of specific hormone recptors. Fractions, 1 ml per 3 minutes, were collected and the concentration of Luteinzing Hormone was determined by radioimmunoassay. NIAMD radioimmunoassay kits were used for the Luteinizing Hormone and Follicle Stimulating Hormone assays. The superfusion data was analyzed by the computer program of Csernus and Schally (1985).

EXAMPLE 8

GnRH analogs

The following GnRH analogs were used herein to illustrate the novel effects of the GnRH-III as demonstrated in the present invention: (1) Buserelin: [D-Ser(tBu)$^6$,desGly$^{10}$-ethylamide]GnRH; (2) Ovurelin: [D-Phe$^6$,desGly$^{10}$-ethylamide]GnRH; (3) MI-1544: [Ac-D-Trp$^{1,3}$, D-Cpa$^2$, D-Lys$^6$, D-Ala$^{10}$]GnRH; (4) SB-30: [Ac-D-Nal$^1$, D-p-Cl-Phe$^2$, D-Trp$^3$, D-Cit$^6$, D-Ala$^{10}$]GnRH; and (5) TH-332: [B-Asp(α-diethylamide$^6$],Gln$^8$)GnRH.

EXAMPLE 9

Cell-damaging effects of the GnRH-III

Figure 2:
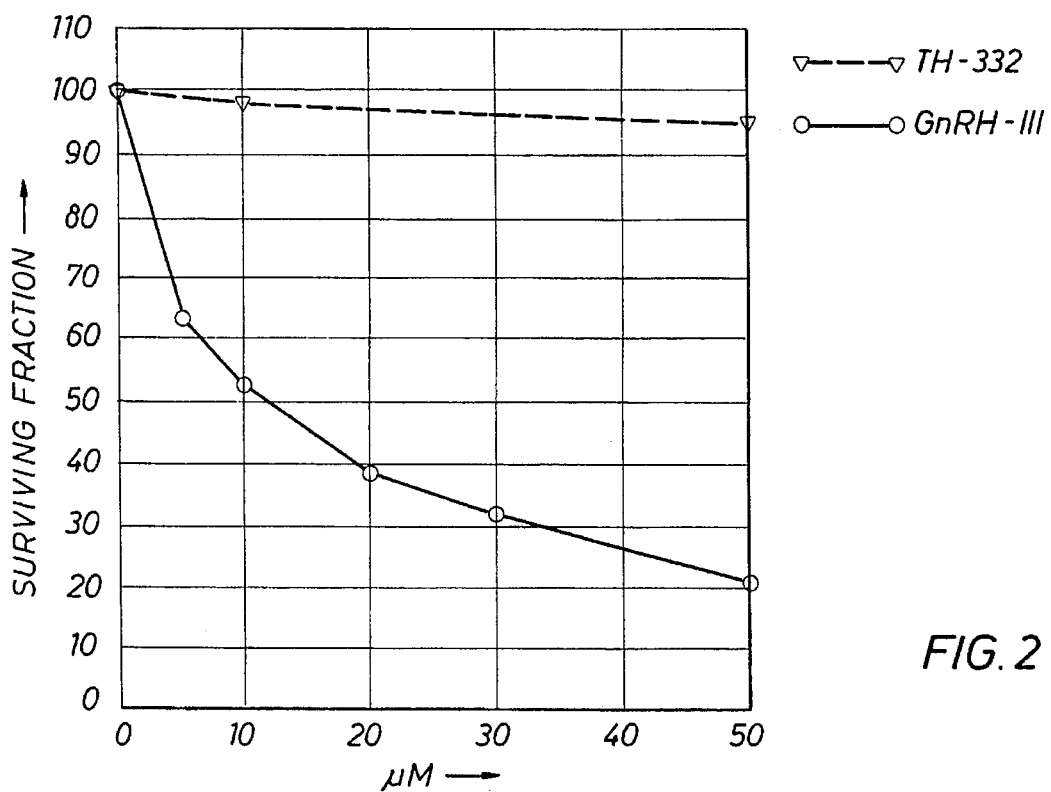
FIG. 2 shows the dose-response curves of MDA-MB-231 cells (10% FCS) treated with GnRH analogs.

The cell-damaging effects of the GnRH-III on MCF-7 and MDA-MB-231 cell lines are shown in FIGS. 1 and 2, respectively. For comparison, the effect of the chicken GnRH, TH-332 is also included. As is clearly shown on FIGS. 1 and 2, GnRH-III inhibited colony formation on both the MCF-7 and MDA-MB-231 cell lines. Cell surviving fractions at 50 μM dose were 35.3% and 21.8% for MCF-7 and MDA-MB-231 cell lines, respectively. TH-332 did not inhibit colony formation in the same dose range.

EXAMPLE 10

Antiproliferative effects of GnRH-III

Figure 3:
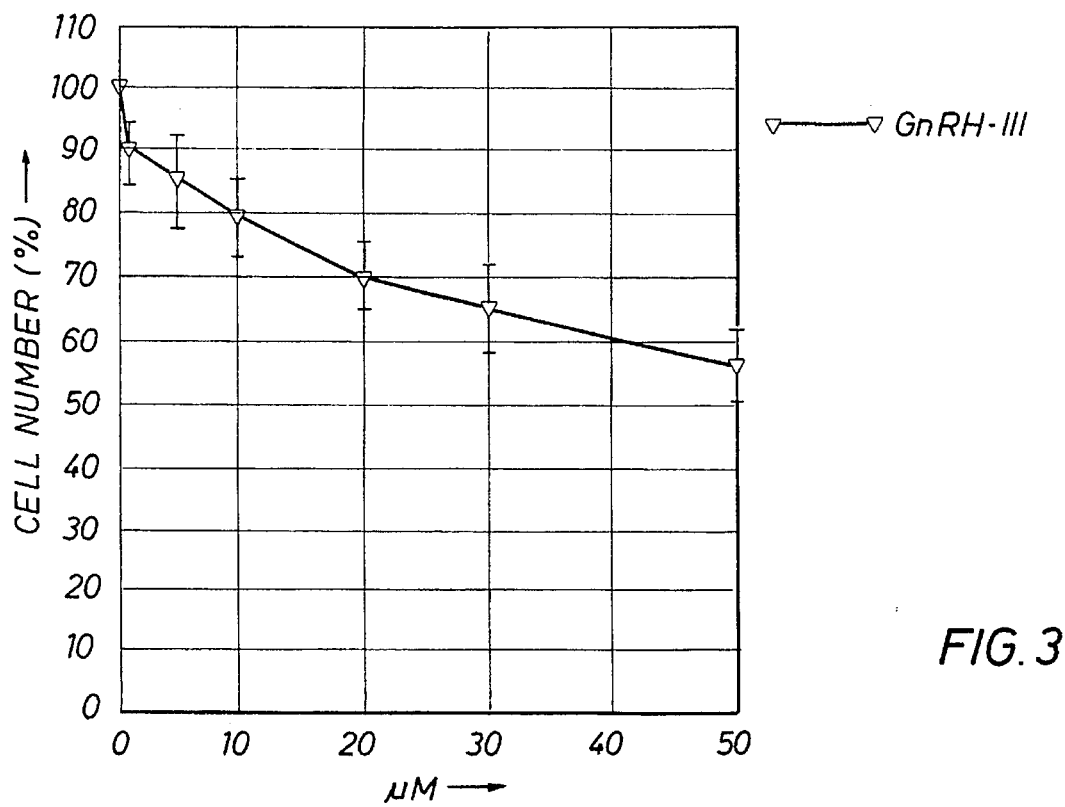
FIG. 3 shows the antiproliferative effect of GnRH-III treatment on MDA-MB-231 (10% FCS) cell line.
Figure 4:
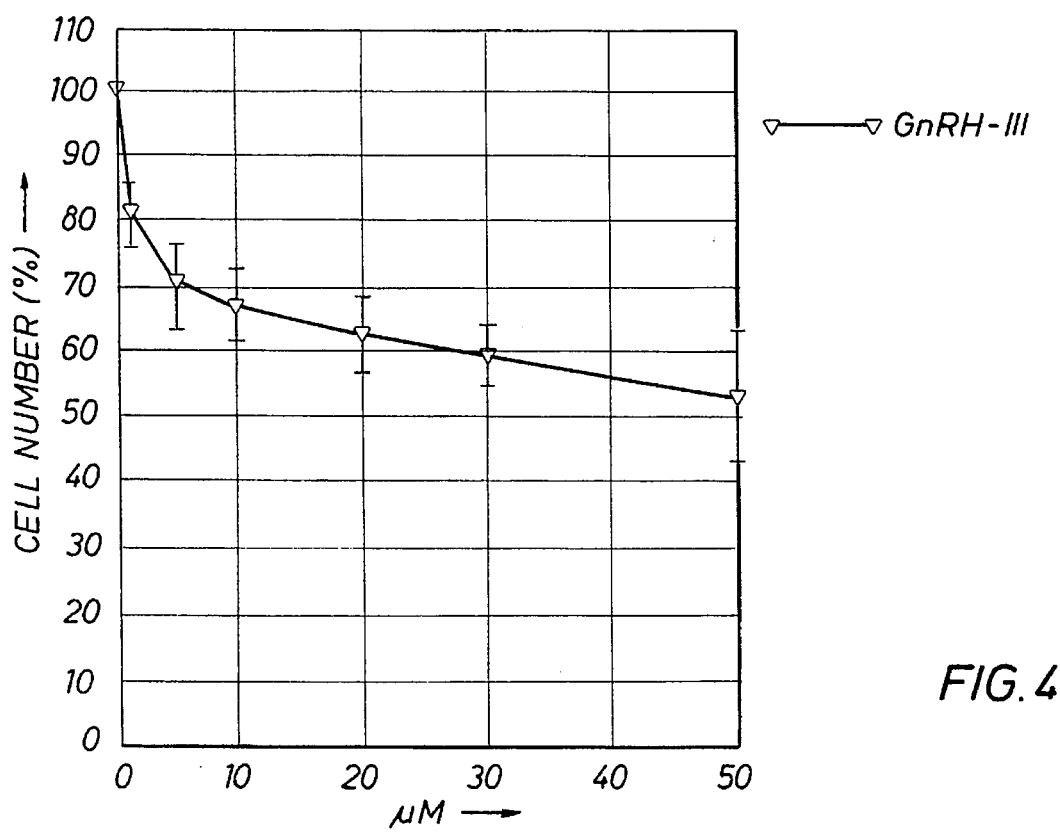
FIG. 4 shows the antiproliferative effect of GnRH-III treatment on MCF-7 (10% FCS) cell line.
Figure 5:
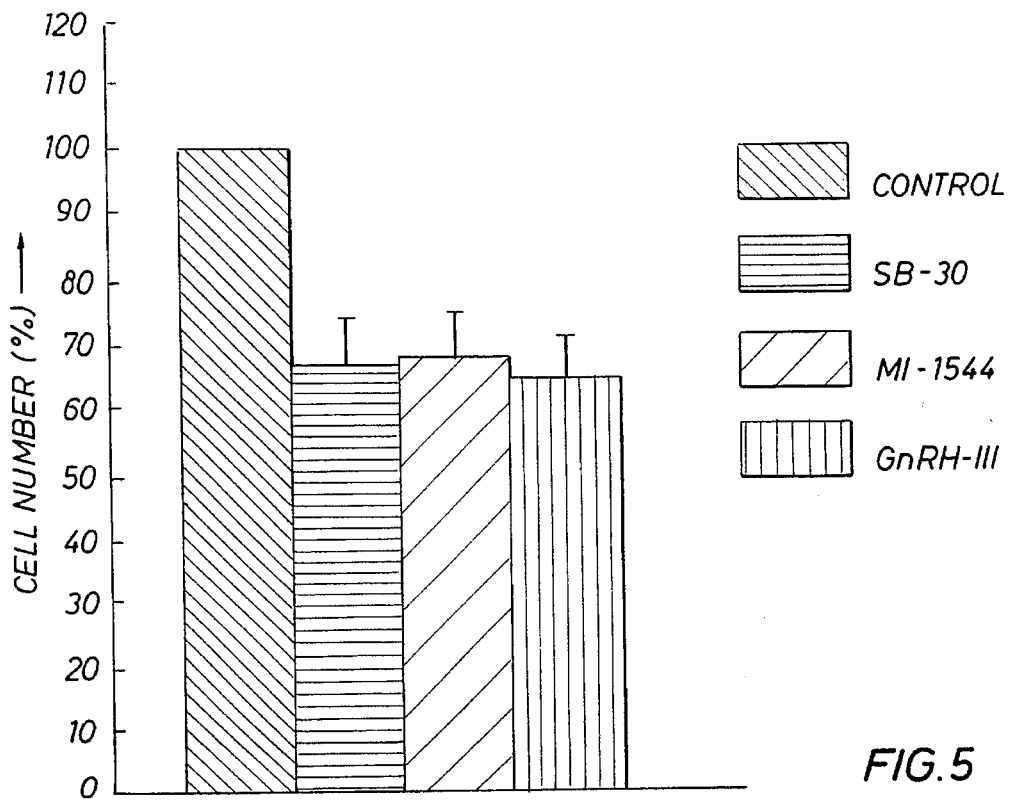
FIG. 5 shows the antiproliferative effect of GnRH analog treatment of the MDA-MB-231 (10% FCS) cell line at a dose of 30 µM.
Figure 6:
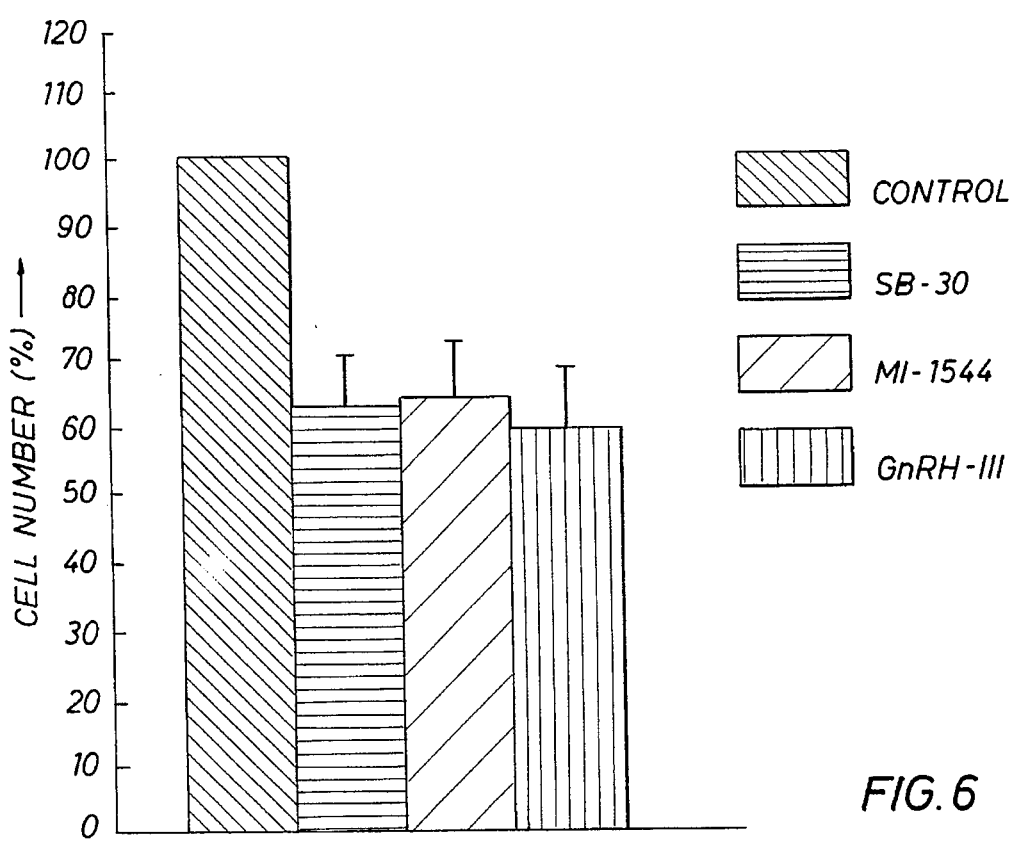
FIG. 6 shows the antiproliferative effect of GnRH analog treatment of the MCF-7 (10% FCS) cell line at a dose of 30 µM.

The antiproliferative effects of GnRH-III on MDA-MB-231 and MCF-7 cell lines are shown in FIGS. 3 and 4, respectively. Inhibition of cell proliferation was 40% on both cell lines at the 50 μM dose. For comparison, the antiproliferative effect of two GnRH antagonists, SB-30 and MI-1544, together with GnRH-III at 30 μM concentration is shown in FIG. 5 and FIG. 6. GnRH-III had similar antiproliferative effect as that of the two antagonists on both cell lines.

EXAMPLE 11

Chemical Castration Effects

In the in vivo assay of ovulation in rats, GnRH-III had no influence on ovulation at doses of $10^{-9}$ to $10^{-7}$M, which are effective doses in case of human GnRH. GnRH-III did not change histology of ovary after repeated injections. In the in vitro assay using superfused rat pituitary cell system, GnRH-III was found to be neither agonist, nor antagonist in mammalian pituitary gland at doses of $10^{-9}$ to $10^{-7}$M.

The present invention discloses the discovery of specific in vitro anticancer activity of GnRH-III on human breast cancer cell lines. The anticancer activity of GnRH-III was found to surpass that of the well known agonists Buserelin, Decapeptyl and Ovurelin, and to approximate that of the antagonists SB-30 and MI-1544. GnRH-III produced a 40% inhibition of human breast cancer cell proliferation and 65–80% decrease in cloning efficiency at 30 μM. In contrast to other synthetic GnRH analogs with anticancer activity, GnRH-III contains only L-amino acids. This is especially remarkable, because the D-amino acid replacements were regarded as the main basis for the stable conformation of many of the previous synthetic GnRH compounds, which play a role in binding properties.

The chemical castration effect of GnRH-III in rat pituitary gland using the superfused rat pituitary cell system was examined. GnRH, at doses $10^{-9}$–$10^{-7}$M did not induce Luteinizing Hormone (LH)-release, but neither did it inhibit the LH-release induced by native GnRH. GnRH-III did cause LH release at relatively high ($10^{-6}$ M) concentration. GnRH-III, in mammlian pituitary gland, was found to be neither agonist, nor antagonist.

The inhibitory effect of GnRH-III on ovulation was examined at doses $10^{-9}$–$10^{-7}$M in female rats. Repeated injections of GnRH-III did not change the histological character of ovary. In rats, GnRH-III did not influence the function of gonads.

In summary, GnRH-III is a natural decapeptide hormone of Lamprey origin, containing only L-amino acids. GnRH-III has a direct anticancer activity. GnRH-III decreases both colony formation and diminishes cell proliferation. Most importantly, unlike prior art Gonadotropin Releasing Hormone analogs, GnRH-III does not influence gonadal function. Taken together, these unexpected properties of GnRH-III establish its desirability as a selective in vivo anticancer agent against breast tumors is humans.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting the proliferation of mammary tumor cells, comprising the step of administering a pharmacologically effective dose of the pharmaceutical composition of Gonadotropin Releasing Hormone-III to an human in need of such treatment.

2. The method of claim 1, wherein said dose is from about 0.002 mg/kg to about 0.02 mg/kg.

3. A method of treating a mammary carcinoma in an human without significant corresponding loss of gonadal function, comprising the step of administering to said human a pharmacologically effective dose of Gonadotropin Releasing Hormone-III.

4. The method of claim 3, wherein said dose is from about 0.002 mg/kg to about 0.02 mg/kg.

* * * * *